(12) United States Patent
Xi et al.

(10) Patent No.: US 10,379,098 B2
(45) Date of Patent: Aug. 13, 2019

(54) RATING EVALUATION METHOD FOR GROUNDWATER POLLUTION SOURCE INTENSITY

(71) Applicant: CHINESE RESEARCH ACADEMY OF ENVIRONMENTAL SCIENCES, Beijing (CN)

(72) Inventors: Beidou Xi, Beijing (CN); Juan Li, Beijing (CN); Ningqing Lv, Beijing (CN); Da An, Beijing (CN); Yang Yang, Beijing (CN); Yue Wang, Beijing (CN); Jun Tang, Beijing (CN)

(73) Assignee: Chinese Research Academy of Environmental Sciences, Beijing (CN)

( * ) Notice: Subject to any disclaimer, the term of this patent is extended or adjusted under 35 U.S.C. 154(b) by 0 days.

(21) Appl. No.: 15/487,346

(22) Filed: Apr. 13, 2017

(65) Prior Publication Data
US 2017/0328878 A1 Nov. 16, 2017

(30) Foreign Application Priority Data
May 13, 2016 (CN) .......................... 2016 1 0320234

(51) Int. Cl.
*G06F 11/30* (2006.01)
*G01N 33/18* (2006.01)

(52) U.S. Cl.
CPC .................... *G01N 33/18* (2013.01)

(58) Field of Classification Search
CPC ..................................................... G01N 33/18
See application file for complete search history.

(56) References Cited

U.S. PATENT DOCUMENTS

2010/0024296 A1\* 2/2010 Lazarus ............ G06Q 30/0202
47/58.1 SC

FOREIGN PATENT DOCUMENTS

| CN | 105184095 | 12/2015 |
| CN | 105427013 | 3/2016 |

OTHER PUBLICATIONS

Li et al., Method for screening prevention and control measures and technologies based on groundwater pollution intensity assessment, Science of the Total Environment, 551-552(2016) 143-154 (Year: 2016).\*

(Continued)

*Primary Examiner* — Phuong Huynh
(74) *Attorney, Agent, or Firm* — Knobbe, Martens, Olson & Bear, LLP

(57) ABSTRACT

A rating evaluation method for groundwater pollution source intensity, including: determining pollution source characteristic indices, and weights and scores thereof, according to the type, the discharge mode, the existence time, and the like of a groundwater pollution source; determining an vadose zone antifouling property index and an vadose zone vulnerability index and scores thereof according to vadose zone characteristics; determining a rating evaluation index system for groundwater pollution sources by combining the pollution source characteristic indices with the vadose zone antifouling property index and the vadose zone vulnerability index; and establishing a rating evaluation method for groundwater pollution source intensity and evaluating the groundwater pollution source intensity. The evaluation method comprehensively considers pollution source characteristics and vadose zone characteristics to accurately reflect source intensities of groundwater pollutants and protect groundwater, and may provide a scientific basis to allow for (Continued)

more scientific and rational protection and management of groundwater.

20 Claims, 2 Drawing Sheets

(56) References Cited

OTHER PUBLICATIONS

Zuoshen Sang, A discussion of groundwater vulnerability assessment methods, Earth Science Frontiers, Apr. 2005, vol. 12 Suppl, p. 003-013.
Jian Wang et. al, Assessment of Shallow Groundwater Vulnerability in Taiyuan Basin, Chinese Journal of Underground Space and Engineering, vol. 7, Feb. 2011, p. 199-206.
Juan Li et. al, Study on groundwater pollution source intensity rating assessment method of typical contaminated sites, Chinese journal of Environmental Engineering, vol. 8, No. 11, Nov. 2014, p. 4726-4736.
Office Action and English Translation dated Feb. 7, 2018 for Chinese Patent Application No. 201610320234.3 in 15 pages.
Li et al., Method for screening prevention and control measures and technologies based on groundwater pollution intensity assessment, Science of the Total Environment, 551-552 (2016) 143-154.
Office Action received in Chinese Application No. 201610320234.3, dated Jan. 3, 2019.

\* cited by examiner

RATING EVALUATION METHOD FOR GROUNDWATER POLLUTION SOURCE INTENSITY

CROSS-REFERENCE TO RELATED APPLICATIONS

The present disclosure claims the priority of Chinese Patent Application No. 201610320234.3, filed on May 13, 2016, which is incorporated by reference herein in its entirety.

BACKGROUND

Field

This disclosure relates to the field of water environment protection, and more specifically to a rating evaluation method for groundwater pollution source intensity.

Description of the Related Art

As the society continuously develops, groundwater pollution becomes an unnegligible problem of pollution and brings about great health risk to the society and the public. Among others, how to scientifically and effectively manage groundwater resources becomes a particularly important problem.

In order to be able to effectively manage groundwater resources, it is required to first determine groundwater pollution source intensity and the hazard level to which it contributes. Since groundwater pollution is greatly influenced by discharge of pollution sources, treatment measures, and different geological structures at various locations, the scientific and rational evaluation of groundwater pollution source intensity could be achieved only if comprehensive consideration is made.

With respect to a rating evaluation method for groundwater pollution source intensity, an evaluation index system and a technical method for practical situations of groundwater pollution source intensity are required to be established, according to characteristics of groundwater pollution source types, distributions, pollutant compositions, hydrogeological conditions, and environmental influences. This would provide scientific bases for utilization and management of land resources, control of groundwater pollution, overall planning and management of economic regions, etc. At present, however, studies in these fields are still deficient.

SUMMARY

In view of this, an object of this disclosure is to provide a rating evaluation method for groundwater pollution source intensity, so as to provide a scientific basis for classified prevention and control and overall management of groundwater pollution source.

In order to achieve the object described above, this invention provides a rating evaluation method for groundwater pollution source intensity, comprising:

step 1: determining pollution source characteristic indices as well as weights and scores thereof, wherein the pollution source characteristic indices measure the magnitude of the potential of a pollution source for outputting pollution, the weights of the pollution source characteristic indices are used to evaluate the relative magnitude of the "contribution" of the pollution source characteristic indices to groundwater pollution, and performing the evaluation of pollution source hazard using an overlay and index method;

step 2: determining vadose zone characteristic indices and scores thereof, wherein the vadose zone characteristic indices include an vadose zone antifouling property index and an vadose zone vulnerability index, and performing evaluation of vadose zone resistance;

step 3: with respect to an field not considering the vadose zone antifouling property, directly using the rating evaluation result of pollution source hazard obtained in step 1 as a rating evaluation result of the groundwater pollution source intensity, without performing step 2; with respect to an field considering the vadose zone antifouling property, performing the evaluation of pollution source hazard of step 1 and the evaluation of vadose zone resistance of step 2 respectively, and combining the two evaluation results by a matrix method, to obtain a result of rating evaluation of the groundwater pollution source intensity.

In one embodiment, a modified. Nemerow index method is employed for the pollution factor comprehensive evaluation index in the evaluation of pollution source hazard, and the concentration, toxicity, mobility, and degradability of pollutants are comprehensively considered.

In one embodiment, the vadose zone antifouling property of a polluted field is preferentially evaluated in the evaluation of vadose zone resistance, to predict whether the vadose zone effect is considered in the evaluation of groundwater pollution source intensity in the field or not.

Based on the technical solutions described above, the pollution source characteristics and the vadose zone characteristics are comprehensively considered in the rating evaluation method for groundwater pollution source intensity of this disclosure, therefore, the method of this disclosure can provide a scientific basis to classify fields of groundwater pollution and allow for more scientific and rational protection and management of groundwater.

DETAILED DESCRIPTION

In order to enable objects, technical solutions, and advantages of this disclosure to be more clearly understood, this disclosure will be further illustrated in details in conjunction with specific embodiments and with reference to accompanying drawings.

The rating evaluation of groundwater pollution source intensity is a key technique in establishing the whole process system of prevention and control of groundwater pollution, and is mainly applicable for analyzing and determining groundwater pollution source intensity.

This disclosure provides a rating evaluation method for groundwater pollution source intensity, which constructs an evaluation index system for groundwater pollution source intensity comprehensively considering pollutant characteristics and vadose zone characteristics in an field, wherein, a modified Nemerow pollution index method and an improved DRMK model are used in evaluations of pollutant characteristics and vadose zone characteristics respectively, pollution source hazard and vadose zone resistance are rated by use of an overlay and index method, and finally a rating evaluation method for groundwater pollution source intensity is established.

1. Rating Evaluation Index System for Groundwater Pollution Source Intensity

Figure 1:
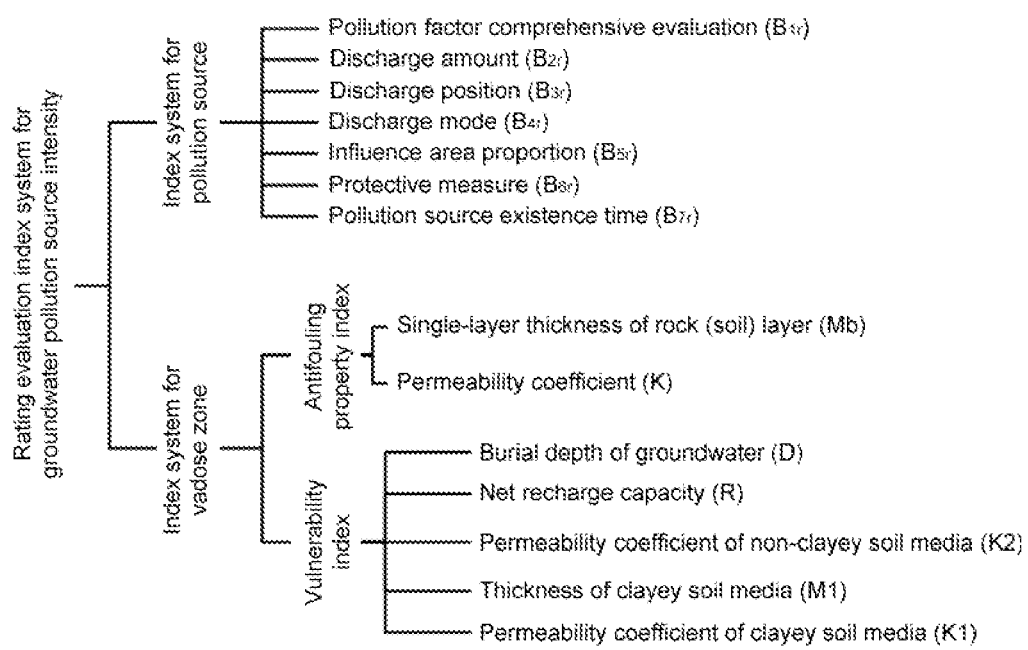
FIG. 1 is the rating evaluation index system for groundwater pollution source intensity of this disclosure.

With respect to the evaluation index system for groundwater pollution source intensity, two aspects, which are pollution source characteristics and vadose zone characteristics, are mainly considered. The indices such as discharge amount, discharge mode, and the like of a pollution source are mainly considered for pollution source characteristics, and the indices such as antifouling property and vulnerability of vadose zone are mainly considered for vadose zone characteristics. A particular evaluation index system for groundwater pollution source intensity is shown in FIG. 1.

2. Rating Evaluation Method for Groundwater Pollution Source Intensity

Figure 2:
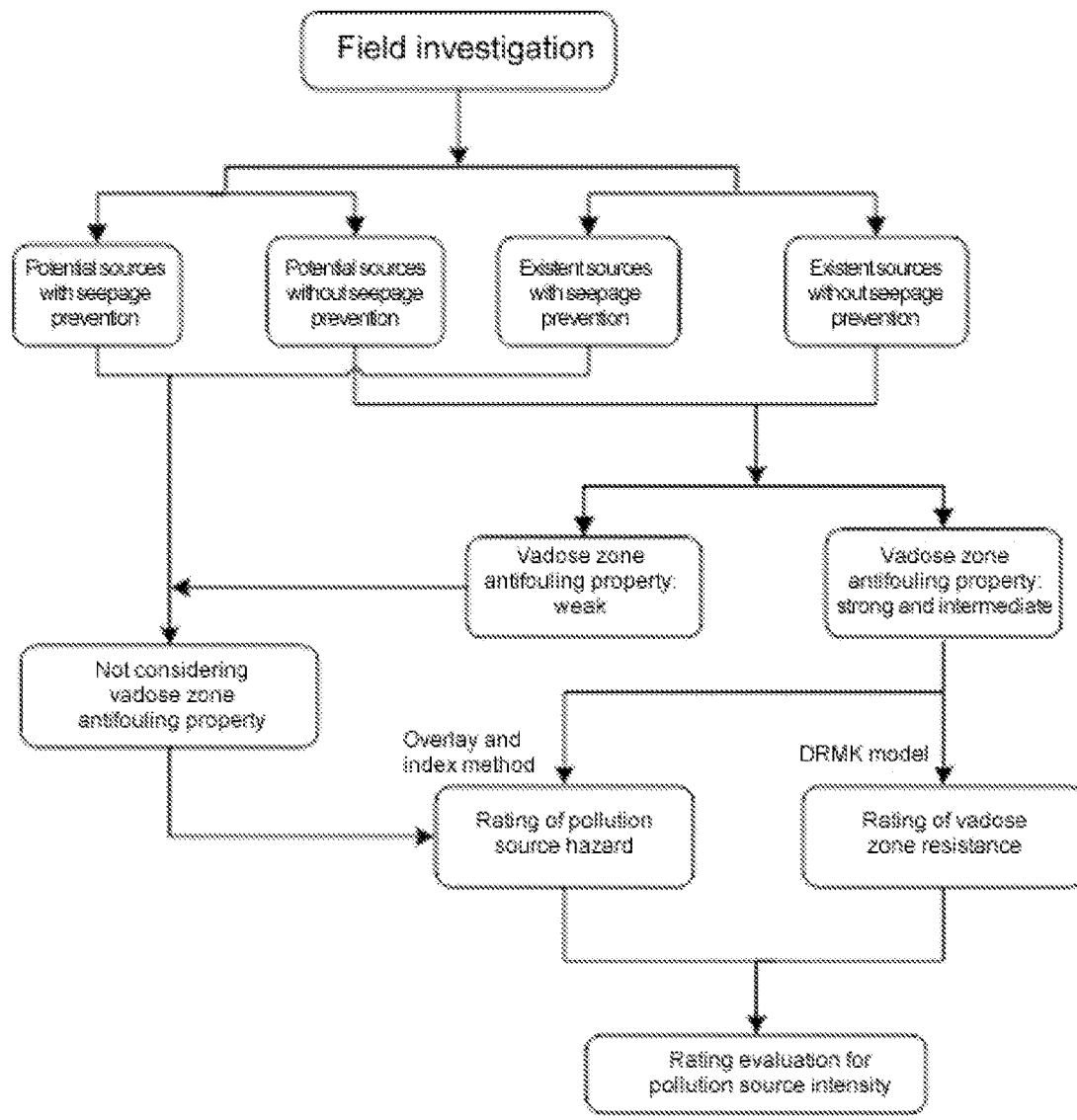
FIG. 2 is a schematic flow chart of the rating evaluation method for groundwater pollution source intensity of this disclosure.

Based on the result of pollution source classification, and according to whether the fields where potential pollution sources and existent pollution sources are located have seepage prevention measures or not, the practical polluted fields are divided into four major types: potential pollution sources with seepage prevention, potential pollution sources without seepage prevention, existent pollution sources without seepage prevention, and existent pollution sources with seepage prevention. A rating evaluation system is established by using these four major types of pollution sources as basic objects for evaluation, and a particular process flow of evaluation is shown in FIG. 2.

3. Study on Groundwater Pollution Source Characteristics 3.1. Weights and Scores of Indices The pollution source characteristic indices measure the magnitude of the potential of a pollution source for outputting pollution. The weight of an index is the magnitude of the contribution of an evaluation factor to groundwater pollution, and a greater weight means a relatively greater risk of groundwater pollution by the evaluation factor. According to the analytic hierarchy process, a judging matrix is established by using a 9-level rating scale method proposed by Saaty, and weighted values of respective indices are rationally determined so as to achieve the object of accurate evaluation for pollution sources. Particular weights of groundwater pollution source indices are shown in Table 1. After the weights of groundwater pollution source indices are determined, respective indices are scored according to the practical situation of a field.

The hazard of a pollution source is determined by comprehensive factors such as the type, the discharge mode, the existence time, and the like of the pollution source. The pollution factor comprehensive evaluation index ($B_{1r}$) comprehensively considers the factors such as toxicities, mobilities, degradabilities, and the like of different pollution factors in a pollution source with respect to the environment. The discharge mode mainly depends on whether a pollution source is treated and the degree of treatment. The influence area proportion refers to a percentage of the area covered by an influence radius relative to the total area of the evaluation region. Influence area proportions of industrial residue piles and agricultural sources are calculated with actual polluted areas. Since the influence ranges of dot-like and linear potential pollution sources such as seepage pits, sewage rivers, etc., are difficult to be obtained in data collection and actual investigation, the influence radius of dot-like potential pollution sources such as seepage pits may be set to be 200 m. and the influence range of linear potential pollution sources such as rivers may be set to 100 m, according to literature research.

Particular weights and scores of groundwater pollution source indices are shown in Table 2.

TABLE 1

Weights of groundwater pollution source indices

| Name | Pollution factor comprehensive evaluation ($B_{1r}$) | Discharge amount ($B_{2r}$) | Discharge position ($B_{3r}$) | Discharge mode ($B_{4r}$) | Influence area proportion ($B_{5r}$) | Protective measure ($B_{6r}$) | Existence time ($B_{7r}$) |
|---|---|---|---|---|---|---|---|
| Weight | 0.22 | 0.17 | 0.16 | 0.1 | 0.09 | 0.12 | 0.14 |

TABLE 2

Scores of groundwater pollution source indices

| Pollution factor comprehensive evaluation | | Discharge amount ($\times 10^4 m^3/a$) | | Discharge position | | Discharge mode | | Influence area proportion | | Protective measure | | Existence time | |
|---|---|---|---|---|---|---|---|---|---|---|---|---|---|
| <0.8 | 2 | Q ≤ 1 | 1 | Ground surface | 6 | Cyclically used after water treatment or discharged into municipal pipelines | 1 | ≤0.1% | 2.5 | Sealed | 1 | ≤1 | 1 |
| 0.80-2.50 | 4 | 1 < q ≤ 10 | 3 | Middle of vadose zone | 8 | | 1 | 0.1%~1% | 5 | Partly sealed | 5 | 1-5 | 3 |
| 2.50-4.25 | 6 | 10 < q ≤ 30 | 5 | Bottom of vadose zone | 10 | Discharged with standard met after treatment | 4 | 1%~10% | 7.5 | Exposed | 10 | 5-10 | 5 |
| 4.25-7.2 | 8 | 30 < q ≤ 60 | 7 | | | Discharged with standard not met after treatment | 8 | 10%~100% | 10 | | | 10-20 | 7 |
| >7.20 | 10 | Q > 60 | 10 | | | Directly discharged | 10 | | | | | >20 | 10 |

3.2. Pollution Factor Comprehensive Evaluation ($B_{1r}$)

At present, as for the evaluation of groundwater pollution sources, a method for averaging by equivalent standard pollution loading is typically used. For a case of groundwater in a region where the content of one pollutant is relatively high while the contents of other pollutants are all relatively low, evaluation results of the above-mentioned method cannot reflect the actual pollution condition of the groundwater environment. Nemerow pollution index method is a weighted-type multi-factor environment quality index method which takes the extremum (or referred to as the outstanding maximum) into account as well. This method can well highlight the effect of extremum, and the application thereof in the evaluation of groundwater pollution source intensity of a polluted field may effectively fill the blanks in studies.

When the Nemerow index method is used in the evaluation of groundwater pollution source intensity, toxicities, mobilities, and degradabilities of different pollution factors with respect to the environment will be considered, and by adding a weighting factor, different pollution factors at the same quality level are differently treated.

A conventional calculation equation of Nemerow comprehensive pollution index is as follows:

$$P_i = \frac{C_i}{C_{0i}} \quad (1)$$

$$P_{comprehensive} = \sqrt{\frac{P_{iave}^2 + P_{imax}^2}{2}} \quad (2)$$

in the equation, $P_i$ is an evaluation value of an $i^{th}$ kind of pollution factor; $c_i$ is an actual concentration value of the $i^{th}$ kind of pollution factor, mg/l; $c_{0i}$ is a standard value of a $j^{th}$-class evaluation standard of the $i^{th}$ kind of pollution factor, mg/l; $P_{iave}$ is the average value of evaluation values of n kinds of pollution factors; $P_{imax}$ is the maximum of the evaluation values of n kinds of pollution factors; and $P_{comprehensive}$ is a Nemerow comprehensive index of the $j^{th}$-class standard.

A modified Nemerow pollution index method considers the weight $a_i$ of each pollution factor in evaluation, and introduces $P'_{weighted\ average}$ to replace $P_{iave}$.

$$P_{comprehensive} = \sqrt{\frac{P'^2_{weighted\ average} + P_{imax}^2}{2}} \quad (3)$$

$$P'_{weighted\ average} = \frac{\sum_{i=1}^{n}(P_i \times a_i)}{n} \quad (4)$$

Wherein, the weighted value $a_i$ of pollution factor is determined as follows.

Generally, the contributions of various pollution factors to the hazard level of groundwater are different, among others, toxicity (T), mobility (M), degradability (D), and the like of a pollution factor are mainly considered in the weight of each pollution factor. The weights of the three factors are 0.6, 0.2, and 0.2 respectively, as calculated by analytic hierarchy process, and the determination of sequential values of these three factors are shown in Table 3. By calculating the pollution factor attribute $l_i$ (equation 5), the calculation of the weighted value $a_i$ of the pollution factor is accomplished (equation 6).

TABLE 3

Determination of sequential values of pollution factors

| Name | Toxicity | Mobility | Degradability |
|---|---|---|---|
| Sequence description | C0i values of various pollution factors are arranged from small to large, and are sequentially numbered. That is, as the C0i becomes greater, the influence on groundwater becomes smaller and the sequential value becomes greater. (positive-sequence arrangement) | The mobility of a pollution factor relies on lgKoc value. A greater value means that the migration of this pollutant is more difficult, the influence on groundwater becomes smaller, and the sequential value becomes greater. (positive-sequence arrangement) | The degradability of a pollution factor relies on the half-life. As the half-life becomes longer, the influence on groundwater becomes greater and the sequential value becomes smaller. (negative-sequence arrangement) |

$$l_i = 0.6T_i + 0.2M_i + 0.2D_i \quad (5)$$

In the equation, $T_i$, $M_i$, and $D_i$ represent sequential values of toxicity, mobility, degradability of an $i^{th}$ kind of characteristic pollutant in the pollution source, respectively.

$$a_i = \frac{l_{max}/l_i}{\sum_{i=1}^{n} l_{max}/l_i} \quad (6)$$

In the equation, $a_i$ is a weighted value of an $i^{th}$ kind of pollution factor; $l_{max}$ is a weighted evaluation value of the maximum characteristic pollutant in n kinds of pollution factors.

4. Study on Vadose Zone Characteristics

4.1. Vadose Zone Antifouling Property Index and Score

For a built project without seepage prevention measures, according to rock (soil) single-layer thickness and permeability coefficient of vadose zone thereof, the vadose zone antifouling property is classed into three levels, which are strong, intermediate, and weak. Particular reference indices are shown in Table 4.

TABLE 4

Rating of vadose zone antifouling property

| Rating | Permeability of vadose zone rock (soil) | Score |
|---|---|---|
| Strong | Rock (soil) layer has a single-layer thickness Mb ≥ 1.0 m, a permeability coefficient K ≤ $10^{-7}$ cm/s, and the distribution is continuous and stable. | 1 |
| Intermediate | Rock (soil) layer has a single-layer thickness 0.5 m ≤ Mb < 1.0 m, a permeability coefficient K ≤ $10^{-7}$ cm/s, and the distribution is continuous and stable. Rock (soil) layer has a single-layer thickness Mb ≥ 1.0 m, a permeability coefficient $10^{-7}$ cm/s < K ≤ $10^{-4}$ cm/s, and the distribution is continuous and stable. | |
| Weak | Rock (soil) layer does not satisfy the conditions of "strong" and "intermediate" described above. | 0 |

4.2. Vadose Zone Vulnerability Index and Score

The DRASTIC method is proposed by EPA, U.S., and can be used to evaluate phreatic aquifers and confined aquifers. This method has been commonly used in Western countries such as the United States, Canada, South Africa, European Union countries, etc. According to practical situations in China, Zuoshen Zhong has proposed a DRTA model to evaluate the vulnerability of a phreatic aquifer and a DLCT model to evaluate the vulnerability of a confined aquifer, on the basis of DRASTIC. The main object to be evaluated in this disclosure is a shallow aquifer, and a DRMK model, which combines the DRTA model and study results of vadose zone antifouling property, is used as a vadose zone vulnerability evaluation tool. Particular weights and scores in this model are shown in Tables 5 and 6.

TABLE 5

Evaluation indices and weights

| Index | Burial depth of groundwater (D) | Net recharge capacity (R) | Thickness of clayey soil media (M1) | Permeability coefficient of clayey soil media (K1) | Permeability coefficient of non-clayey soil media (K2) |
|---|---|---|---|---|---|
| Weight | 1 | 2 | 4 | 5 | 3 |

5. Steps of Rating Evaluation 5.1. Rating of Evaluation of Pollution Source Hazard Pollution source hazard is evaluated by an overlay and index method, as particularly shown in equation (7), based on the calculation of pollution factors of groundwater pollution sources as well as the weights and the scores of respective parameters described above. With an unequal interval method, calculation results of the equation (7) in a value range of 0-10 are divided into 3 levels: level I when B≤4.0; level II when 4.0≤B<7.0; and level III when B≥7.0.

$$B=0.22B_{1r}+0.17B_{2r}+0.16B_{3r}+0.1B_{4r}+0.9B_{5r}+0.12B_{6r}+0.14B_{7r} \quad (7)$$

In the equation, $B_{ir}$ is a score of each parameter.

As the B value becomes greater, the groundwater pollution source hazard becomes higher and the evaluation level becomes higher.

5.2. Rating of Evaluation of Vadose Zone Resistance

The rating of vadose zone comprehensive evaluation will comprehensively consider the factors in two aspects, which are antifouling property and vulnerability of vadose zone, in which, the vadose zone antifouling property of a polluted field is preferentially evaluated in the evaluation of vadose zone resistance, to predict whether the vadose zone effect is considered in the evaluation of groundwater pollution source intensity in the field or not. In the case where the vadose zone effect is considered, the score of vadose zone antifouling property (V), as a factor, is introduced to the calculation of vadose zone vulnerability index (DI), and the score of V is determined according to Table 4. In the calculation of the vadose zone vulnerability index, the score of vadose zone media thickness (T) is related to the thickness and the type of vadose zone media (R). It is not rational to give the same score value to different media with the same thickness, and thus the score value of T is multiplied by the score value of R in addition to being multiplied by the weight. The calculation of vadose zone comprehensive evaluation index (DI') is shown in equation (8). The DI' value ranges from 15 to 150, and the evaluation of vadose zone resistance is divided into 3 levels: level I when DI'<70; level II when 70≤DI'<120; level III when DI'>120.

$$DI'=V\times(1\times D+2\times R+4\times M+5\times K1+3\times K2) \quad (8)$$

In the equation, V, D, R, M, K1 and K2 are score values of respective factors.

As the DI' value becomes higher, the vadose zone antifouling property becomes poorer, the vulnerability becomes higher, and the level becomes higher.

TABLE 6

Types and scores of various factors of DRMK model

| Evaluation index | Burial depth of groundwater (D) | Net recharge capacity (R) | Thickness of clayey soil media (M1) | Permeability coefficient of clayey soil media (K1) | Permeability coefficient of non-clayey soil media (K2) |
|---|---|---|---|---|---|
| 10 | ≤1.5 | >254 | ≤1.6 | $9 \times 10^{-7} \sim 12 \times 10^{-7}$ | $>2.2 \times 10^{-1}$ |
| 9 | 1.5~4.6 | 235~254 | 1.6~3.3 | $8 \times 10^{-7} \sim 9 \times 10^{-7}$ | $2.0 \times 10^{-1} \sim 2.2 \times 10^{-1}$ |
| 8 | 4.6~6.8 | 216~235 | 3.3~5.0 | $7 \times 10^{-7} \sim 8 \times 10^{-7}$ | $1.8 \times 10^{-1} \sim 2.0 \times 10^{-1}$ |
| 7 | 6.8~9.1 | 178~216 | 5.0~7.8 | $6 \times 10^{-7} \sim 7 \times 10^{-7}$ | $6.0 \times 10^{-2} \sim 1.8 \times 10^{-1}$ |
| 6 | 9.1~12.1 | 147.6~178 | 7.8~13.5 | $5 \times 10^{-7} \sim 6 \times 10^{-7}$ | $2.4 \times 10^{-2} \sim 6.0 \times 10^{-2}$ |
| 5 | 12.1~15.2 | 117.2~147.6 | 10.7~13.5 | $4 \times 10^{-7} \sim 5 \times 10^{-7}$ | $6.0 \times 10^{-3} \sim 2.4 \times 10^{-2}$ |
| 4 | 15.2~22.9 | 91.8~117.2 | 13.5~14.5 | $3 \times 10^{-7} \sim 4 \times 10^{-7}$ | $1.2 \times 10^{-3} \sim 6.0 \times 10^{-3}$ |
| 3 | 22.9~26.7 | 71.4~91.8 | 14.5~15.5 | $2 \times 10^{-7} \sim 3 \times 10^{-7}$ | $6.0 \times 10^{-4} \sim 1.2 \times 10^{-3}$ |
| 2 | 26.7~30.5 | 51~71.4 | 15.5~16.5 | $1 \times 10^{-7} \sim 2 \times 10^{-7}$ | $6.0 \times 10^{-5} \sim 6.0 \times 10^{-4}$ |
| 1 | >30.5 | ≤51 | >16.5 | $<10^{-7}$ | $1.2 \times 10^{-6} \sim 6.0 \times 10^{-5}$ |

5.3. Rating of Evaluation of Groundwater Pollution Source Intensity

The pollution source characteristic and the vadose zone characteristic are required to be comprehensively considered with respect to the evaluation result of groundwater pollution source intensity. This disclosure combines both of the characteristics using a matrix method, to concisely, briefly, and directly indicate the coupled effects of characteristic factors of pollution source and vadose zone on groundwater source intensity. Particular results of rating are shown in Table 7. The higher the level is, the greater the groundwater pollution source intensity is.

TABLE 7

Rating of groundwater pollution source intensity

| Rating of groundwater pollution source intensity | | Rating of pollution source hazard | | |
|---|---|---|---|---|
| | | I | II | III |
| Rating of vadose zone resistance | I | I | I | II |
| | II | I | II | II |
| | III | II | II | III |

EXAMPLES

Field 1: An Informal Refuse Landfill, which has an Existent Pollution Source without Seepage Prevention and Vadose Zone Antifouling Property being "Weak"

An informal refuse landfill was used as an object for study. This informal refuse landfill was an already built project without seepage prevention measures, and was rated for vadose zone antifouling property according to FIG. 2. The vadose zone of the field mainly consisted of sand gravel, and the permeability coefficient of the vadose zone was 0.006 cm/s so the vadose zone antifouling property of this field was "weak" according to Table 4. Therefore, when groundwater pollution source intensity was evaluated, only the groundwater pollution source hazard evaluation was performed, without considering the effect of the vadose zone.

According to monitoring results of landfill refuse percolate, $NH_3$—N 1810 mg/L, Cr 0.222 mg/L, Cd 0.045 mg/L, As 0.0444 mg/L, and Hg 0.00157 mg/L, among others, were selected as main factors in pollution factor comprehensive evaluation. By using class I water quality in the quality standard of groundwater as the standard, the sequences of toxicity, mobility, and degradability of related pollutants were determined. $a_i$ values of $NH_3$—N, Cr, Cd, As, and Hg were 0.09, 0.16, 0.26, 0.20, and 0.29 respectively, as calculated according to equation (5) and equation (6). $P'_{weighted\ average}=7.40$, $P_{imax}=362$, and $P'_{comprehensive}=256$ were further obtained according to equation (3) and equation (4).

The average annual rainfall in the region where this field was located was 480 mm, and the discharge amount of percolate was $3.84\times10^4$ m$^3$/a.

The landfill amount was 1550000 m$^3$, and area in contact with ground was 100000 m$^2$, and the influence area proportion was 79.6%. The service time was ten years, and it has been closed now.

According to Table 2, $P'_{comprehensive}$, discharge amount, discharge position, discharge mode, influence area proportion, protective measures for pollution source, and existence time of pollution source had scores of 10, 3, 8, 10, 10, 10, and 5, respectively.

The pollution source hazard B value was 7.79 as calculated according to equation (7). The rating of the evaluation of pollution source hazard resulted in level III by referring to Table 7. The rating of the evaluation of pollution source hazard was the rating of the evaluation of groundwater pollution source intensity according to FIG. 2. Therefore, the rating of the evaluation of groundwater pollution source intensity was level III.

Field 2: A Stockpile in a Rare Earth Mine Exploitation Project, which has a Potential Pollution Source with Seepage Prevention A rare earth mine exploitation project was used as an object for study. The waste disposal site of this exploitation project was a main pollution source of groundwater, and seepage prevention measures were going to be built in the waste disposal site.

According to the results of a test for identifying the hazard of waste ores, Cu 0.354 mg/L, Cr 0.055 mg/L, Cd 0.0015 mg/L, As 0.0024 mg/L, Pb 0.227 mg/L, and Hg 0.0035 mg/L, among others, were selected as main factors in pollution factor comprehensive evaluation. By using "Identification standards for hazardous wastes—Identification for extraction toxicity" (GB5085.3-2007) and "Integrated wastewater discharge standard" (GB8978-1996) as the standards, the sequences of toxicity, mobility, and degradability of related pollutants were determined. $a_i$ values of Cu, Cr, Cd, As, Pb, and Hg were 0.15, 0.08, 0.2, 0.15, 0.10, and 0.32 respectively as calculated according to equation (5) and equation (6). $P'_{weighted\ average}=0.026326$, $P_{imax}=0.708$, and $P'_{comprehensive}=0.5$ were further obtained according to equation (3) and equation (4).

The area of the waste disposal site was 10000 m$^2$, the average annual rainfall in this region over several years was 1800 mm, and the discharge amount was $1.4\times10^4$ m$^3$/a.

This project had a total floor area of about 340000 m$^2$, and the influence area proportion of the waste disposal site was 3%. The evaluation time was set to be 20a.

According to Table 2, $P'_{comprehensive}$, discharge amount, discharge position, discharge mode, influence area proportion, protective measures for pollution source, and existence time of pollution source had scores of 2, 3, 6, 10, 7.5, 5, and 10, respectively.

The pollution source hazard B value was 5.585 as calculated according to equation (7) and the rating of the evaluation of pollution source hazard resulted in level II. The rating of the evaluation of pollution source hazard was the rating of the evaluation of groundwater pollution source intensity according to FIG. 2. Therefore, the rating of the evaluation of groundwater pollution source intensity was level II.

Field Verification

Evaluation results of groundwater pollution source intensities of three fields were compared to monitoring reports of groundwater of four fields. Particular results are shown in Table 8.

TABLE 8

Field verification

| Field | Rating of evaluation of groundwater pollution source intensity | Monitoring report of groundwater (2013) Class I water quality in "Environment quality standard for groundwater" |
|---|---|---|
| 1 | III | Five pollutants including $NH_3$—N, Cr, Cd, As, and Hg in the groundwater of the field exceeded the standard by 2.9-5 times. |

TABLE 8-continued

Field verification

| Field | Rating of evaluation of groundwater pollution source intensity | Monitoring report of groundwater (2013) Class I water quality in "Environment quality standard for groundwater" |
|---|---|---|
| 2 | II | Six pollutants including Cu, Cr, Cd, As, Pb, and Hg in the groundwater of the field did not exceed the standard. |

As seen from the table, the concentrations of pollutants involved in the evaluation of field 1 exceeded the standard, relatively complying with the result of level III in the rating of the evaluation of groundwater pollution source intensity; and none of the concentrations of pollutants involved in the evaluation of field 2 exceeded the standard, relatively complying with the result of level II in the rating of the evaluation of groundwater pollution source intensity in the field. Therefore, the results of the evaluation models established were acceptable.

The objects, technical solutions, and advantageous effects of this disclosure are illustrated in details by the specific Example described above. It is to be understood that those described above are merely some specific Examples of the invention, but are not intended to limit the invention. All of modifications, equivalent replacements, improvements, and the like, which are within the spirit and the principle of the invention, should be encompassed in the scope protected by this invention.

What is claimed is:

1. A method of prevention and control and overall management of groundwater pollution source, comprising:
    performing a field investigation on a groundwater pollution source, to determine whether a seepage prevention or a potential seepage prevention is present or not;
    performing a rating evaluation of groundwater pollution source intensity, comprising the steps of:
    step 1: determining pollution source characteristic indices, and weights and scores thereof; wherein the pollution source characteristic indices measure the magnitude of the potential of a pollution source for outputting pollution, the weights of the pollution source characteristic indices are used to evaluate the relative magnitude of the contribution of the pollution source characteristic indices to groundwater pollution, and evaluation of pollution source hazard is performed using an overlay and index method;
    step 2: determining vadose zone characteristic indices and scores thereof, wherein the vadose zone characteristic indices include a vadose zone antifouling property index and a vadose zone vulnerability index, and performing evaluation of vadose zone resistance;
    step 3: with respect to a field not considering the vadose zone antifouling property, directly using a result of the rating evaluation of pollution source hazard obtained in step 1 as a result of the rating evaluation of the groundwater pollution source intensity without performing step 2; with respect to a field considering the vadose zone antifouling property, performing the evaluation of pollution source hazard of step 1 and the evaluation of vadose zone resistance of step 2 respectively, and combining two evaluation results to obtain a result of the rating evaluation of the groundwater pollution source intensity; and
    applying a protection or management measure to the groundwater pollution source, according to the result of the rating evaluation of the ground water pollution source intensity.

2. The method according to claim 1, wherein the pollution source characteristic indices in step 1 comprise pollution factor comprehensive evaluation $B_{1r}$, discharge amount $B_{2r}$, discharge position $B_{3r}$, discharge mode $B_{4r}$, influence area proportion $B_{5r}$, protective measure $B_{6r}$, and pollution source existence time $B_{7r}$.

3. The method according to claim 2, wherein the weights of the pollution factor comprehensive evaluation $B_{1r}$, the discharge amount $B_{2r}$, the discharge position $B_{3r}$, the discharge mode $B_{4r}$, the influence area proportion $B_{5r}$, the protective measure $B_{6r}$ and pollution source existence time $B_{7r}$ are 0.22, 0.17, 0.16, 0.1, 0.09, 0.12, and 0.14, respectively.

4. The method according to claim 2, wherein the pollution factor comprehensive evaluation $B_{1r}$ comprises evaluations of concentration, toxicity, mobility, and degradability of pollutants, and the evaluations are performed by a modified Nemerow index method.

5. The method according to claim 4, wherein the modified Nemerow pollution index method has the following calculation formulas:

$$P_{comprehensive} = \sqrt{\frac{P'^2_{weighted\ average} + P^2_{imax}}{2}} \quad (I)$$

$$P'_{weighted\ average} = \frac{\sum_{i=1}^{n}(P_i \times a_i)}{n} \quad (II)$$

$$P_i = \frac{C_i}{C_{0i}} \quad (III)$$

wherein $P_{imax}$ is the maximum of evaluation values of n kinds of pollution factors; $P_{comprehensive}$ is a Nemerow comprehensive index of a $j^{th}$-class standard; $P'_{weighted\ average}$ is a weighted average value of evaluations of n kinds of pollution factors; $P_i$ is an evaluation value of an $i^{th}$ kind of pollution factor; $a_i$ is a weighted value of an $i^{th}$ kind of pollution factor; n is the number of pollution factors; $c_i$ is an actual concentration value of an $i^{th}$ kind of pollution factor; $c_{0i}$ is a standard value of a $j^{th}$-class evaluation standard of an $i^{th}$ kind of pollution factor;
the method for calculating the weighted value $a_i$ of the $i^{th}$ kind of pollution factor is as follows:

$$a_i = \frac{l_{max}/l_i}{\sum_{i=1}^{n} l_{max}/l_i} \quad (IV)$$

$$l_i = 0.6T_i + 0.2M_i + 0.2D_i \quad (V)$$

in the formula, $l_{max}$ is the weighted evaluation value of the maximum characteristic pollutant in n kinds of pollution factors; $l_i$ is a weighted evaluation value of an $i^{th}$ kind of characteristic pollutant; $T_i$, $M_i$, $D_i$ represent sequential values of toxicity, mobility, degradability of an $i^{th}$ kind of characteristic pollutant, respectively.

6. The method according to claim 2, wherein the discharge mode comprises whether a pollution source is treated and the degree of treatment.

7. The method according to claim 2, wherein the influence area proportion refers to a percentage of the area covered by an influence radius of the pollution source relative to the total area of the evaluation region.

8. The method according to claim 2, wherein the influence radius of a dot-like potential pollution source such as a seepage pit is set to be 200 m, and the influence radius of a linear potential pollution source such as a river is set to be 100 m.

9. The method according to claim 1, wherein the evaluation of pollution source hazard using an overlay and index method comprises calculating the pollution source hazard index according to the following formula:

$$B=0.22B_{1r}+0.17B_{2r}+0.16B_{3r}+0.1B_{4r}+0.09B_{5r}+0.12B_{6r}+0.14B_{7r}$$

in the formula, B is a pollution source hazard index, and $B_{1r}$-$B_{7r}$ are scores of pollution factor comprehensive evaluation $B_{1r}$, discharge amount $B_{2r}$, discharge position $B_{3r}$, discharge mode $B_{4r}$, influence area proportion $B_{5r}$, protective measure $B_{6r}$, and pollution source existence time $B_{7r}$, respectively.

10. The method according to claim 9, wherein the result of the calculation of B value ranges from 0 to 10.

11. The method according to claim 1, wherein the vadose zone antifouling property index in step 2 comprises single-layer thickness Mb and permeability coefficient K of vadose zone rock/soil layers.

12. The method according to claim 1, wherein the vadose zone vulnerability index in step 2 is determined by using a DRMK model as an evaluation tool of vadose zone vulnerability on the basis DRASTIC.

13. The method according to claim 12, wherein in the DRMK model, the vadose zone vulnerability index in step 2 comprises five indices, which are burial depth of groundwater D, net recharge capacity R, permeability coefficient of non-clayey soil media K2, thickness of clayey soil media M1, and permeability coefficient of clayey soil media K1.

14. The method according to claim 13, wherein the weights of burial depth of groundwater D, net recharge capacity R, permeability coefficient of non-cohesive soil media K2, thickness of cohesive soil media M1, and permeability coefficient of cohesive soil media K1 are 1, 2, 3, 4, and 5, respectively.

15. The method according to claim 1, wherein in the evaluation of vadose zone resistance in step 2, the vadose zone antifouling property of a polluted field is preferentially evaluated, to predict whether the vadose zone effect is considered in the evaluation of groundwater pollution source intensity or not.

16. The method according to claim 1, wherein a result of the rating evaluation of the vadose zone resistance in step 2 is obtained according to the following method:
vadose zone resistance index DI' is calculated by the following formula:

$$DI'=V\times(1\times D+2\times R+4\times M+5\times K1+3\times K2)$$

in the formula, V is a score value of the vadose zone antifouling property; and D, R, M, K1, and K2 are score values of burial depth of groundwater D, net recharge capacity R, thickness of clayey soil media M1, permeability coefficient of clayey soil media K1, and permeability coefficient of non-clayey soil media K2, respectively.

17. The method according to claim 16, wherein the DI' value ranges from 15 to 150.

18. The method according to claim 1, wherein the procedure of combining two evaluation results as a result of rating evaluation of the groundwater pollution source intensity by a matrix method in step 3 comprises:
dividing the pollution source hazard index B value obtained in step 1 into 3 levels with an unequal interval method: level I when B<4.0; level II when 4.0≤B<7.0; and level III when B≥7.0;
dividing the rating evaluation result of the vadose zone resistance obtained in step 2 into 3 levels: level I when DI'<70; level II when 70≤DI'<120; and level III when DI'>120; and
using the following table

| Rating of vadose zone resistance | Rating of pollution source hazard | Rating of groundwater pollution source intensity |
|---|---|---|
| I | I | I |
|   | II | I |
|   | III | II |
| II | I | I |
|   | II | II |
|   | III | II |
| III | I | II |
|   | II | II |
|   | III | III | to find a corresponding result of the rating evaluation of groundwater pollution source intensity according to the result of the rating evaluation of pollution source hazard and the result of the rating evaluation of vadose zone resistance.

19. The method according to claim 1, wherein polluted fields are divided into four major types: potential pollution sources with seepage prevention, potential pollution sources without seepage prevention, existent pollution sources without seepage prevention, and existent pollution sources with seepage prevention, and the field not considering the vadose zone antifouling property in step 3 comprises: a field of potential pollution sources with seepage prevention, a field of existent pollution sources with seepage prevention, and a field of weak vadose zone antifouling property.

20. A method for classified prevention and control and management of a groundwater pollution source, comprising:
performing rating evaluation on a groundwater pollution source by:
step 1: determining pollution source characteristic indices, and weights and scores thereof; wherein the pollution source characteristic indices measure the magnitude of the potential of a pollution source for outputting pollution, the weights of the pollution source characteristic indices are used to evaluate the relative magnitude of the contribution of the pollution source characteristic indices to groundwater pollution, and evaluation of pollution source hazard is performed using an overlay and index method;
step 2: determining vadose zone characteristic indices and scores thereof, wherein the vadose zone characteristic indices include a vadose zone antifouling property index and a vadose zone vulnerability index, and performing evaluation of vadose zone resistance;
step 3: with respect to a field not considering the vadose zone antifouling property, directly using the evaluation of pollution source hazard obtained in step 1 as a result of the rating evaluation of the groundwater pollution source intensity without performing step 2; with respect to a field considering the vadose zone antifouling property, performing the evaluation of pollution source hazard of step 1 and the evaluation of vadose zone resistance of step 2 respectively, and combining two evaluation results to obtain a result of rating evaluation of the groundwater pollution source intensity; and applying corresponding measures of prevention and control and management to the groundwater pollution source, according to the result of the rating evaluation of the groundwater pollution source.

\* \* \* \* \*